(12) United States Patent
Urban

(10) Patent No.: US 9,351,896 B2
(45) Date of Patent: May 31, 2016

(54) PORTABLE ASEPTIC UNIT AND PROCESS FOR THE ASEPTIC PREPARATION AND ASEPTIC DELIVERY OF DRUGS, DEVICES AND COSMETICS TO HUMANS OR ANIMALS IN AN ASEPTIC ENVIRONMENT

(71) Applicant: Joseph John Urban, Richboro, PA (US)

(72) Inventor: Joseph John Urban, Richboro, PA (US)

( * ) Notice: Subject to any disclaimer, the term of this patent is extended or adjusted under 35 U.S.C. 154(b) by 821 days.

(21) Appl. No.: 13/694,170

(22) Filed: Nov. 5, 2012

(65) Prior Publication Data

US 2014/0123594 A1  May 8, 2014

(51) Int. Cl.
*B65B 55/00* (2006.01)
*A61G 13/10* (2006.01)
*A61G 13/12* (2006.01)

(52) U.S. Cl.
CPC ............ *A61G 13/108* (2013.01); *A61G 13/124* (2013.01)

(58) Field of Classification Search
CPC ............... A61B 19/0248; A61B 2019/025; A61G 13/108; A61G 13/124; A61G 13/12; B65B 55/00; B65B 55/027
USPC ........ 454/49, 66, 187, 188, 189, 370; 53/167, 53/385.1; 248/129; 312/209
See application file for complete search history.

(56) References Cited

U.S. PATENT DOCUMENTS

| | | | | |
|---|---|---|---|---|
| 3,820,536 A * | 6/1974 | Anspach, Jr. | ........ | A61G 13/108 128/202.13 |
| 3,861,894 A * | 1/1975 | Marsh | ....................... | A61L 9/03 261/107 |
| 4,045,192 A * | 8/1977 | Eckstein | ................ | A61G 10/02 261/104 |
| 4,875,696 A * | 10/1989 | Welch | ....................... | B62B 5/04 188/1.12 |
| 6,099,607 A * | 8/2000 | Haslebacher | .......... | F24F 3/1607 55/356 |
| 6,345,873 B1 * | 2/2002 | Kim | .................... | A61B 19/0248 248/68.1 |
| 6,811,593 B2 * | 11/2004 | Hansson | .............. | A61G 13/108 55/356 |
| 6,884,158 B1 * | 4/2005 | Blomqvist | ............. | A61B 19/38 454/189 |
| 7,311,700 B2 * | 12/2007 | Guimaraes | .......... | A61F 9/00804 606/10 |
| 7,806,376 B2 * | 10/2010 | Song | ........................ | A61B 5/00 108/50.01 |
| 2008/0149001 A1 * | 6/2008 | Hodges | .............. | A61B 19/0248 108/6 |
| 2010/0081368 A1 * | 4/2010 | Della Valle | .......... | A61G 13/108 454/66 |

\* cited by examiner

*Primary Examiner* — Gregory Huson
*Assistant Examiner* — Dana Tighe
(74) *Attorney, Agent, or Firm* — MU Patents; Timothy Marc Shropshire

(57) ABSTRACT

The PORTABLE ASEPTIC UNIT is an invention which will provide an aseptic environment at a first location to allow mixing and preparation of aseptic products and then provide an aseptic environment at the site of administration to patient or animal.

4 Claims, 2 Drawing Sheets

PORTABLE ASEPTIC UNIT AND PROCESS FOR THE ASEPTIC PREPARATION AND ASEPTIC DELIVERY OF DRUGS, DEVICES AND COSMETICS TO HUMANS OR ANIMALS IN AN ASEPTIC ENVIRONMENT

FIELD OF THE INVENTION

This invention relates to the field and Pharmacy and more specifically to the preparation and delivery of aseptic drugs to a human or animal under aseptic conditions. These aseptic products are commonly referred to as sterile products, injectables, eye drops, ear drops, parenteral solutions, intravenous injections, intra-arterial injections, intramuscular injections, intra-dermal injections, subcutaneous injections as well as other injections, tablets, capsules, rods, and other objects for insertion into or onto the body of a human or animal.

BACKGROUND OF THE INVENTION

Parenteral and sterile products are usually required to be sterile at the time of injection into or application to the human body. Pharmaceutical manufacturers of Sterile Products must follow a plethora of regulations and current Good Manufacturing Processes such as: 21 CFR 210; 21CFR 211; 21 CFR 11; USP <797>; CGAMP; GLP; GCP; Cleaning Validations; WHO Requirements; Re-Validation Requirements, just to name a few. For parenteral and sterile products, these regulations have a few objectives in common: TO INSURE THAT THE FINISHED PRODUCT IS SAFE FOR HUMAN USE; THAT IT IS EFFECTIVE: and, if it is a sterile product, THAT IT REMAINS STERILE UNTIL ADMINISTRATION TO A HUMAN or ANIMAL.

As professionals, the doctors, nurses, pharmacists, dentists, veterinarians and others who administer injections should maintain the sterility of the product through purchase to administration to a patient.

However, in a multitude of cases, this is not so. Examining the average pharmacy one should be able to observe some, if not most, of the following when an injection is prepared, opened and administered to the next customer or patient in line. The common factors of contamination are, but not limited to: dirt, dust, food, paperwork, contaminated prescriptions, exposed trash, etc. on lab surface; dirt, stains, dust on floors, rug and walls; air vents laden with dust and mold just blowing down on the injection; the professional to administer the injection has exposed hair, hands, nails and lab coat all contributing to contamination; the sink area with filth, rust, sponges, equipment not cleaned and water which may not be fit to drink; direct access to outside in pharmacies with drive-through; customers and patients coughing, spitting, sneezing, blowing their noses, touching and contaminating the areas where the injection is to be compounded, prepared and administered. If the FDA would enter a sterile drug manufacturer with these infractions of cGMPs ongoing, they would certainly issue an FDA483 or FDA Warning Letter. The manufacturing site, may even be shut down and all products produced recalled.

It is just not Pharmacy at fault, many of the same conditions and worse can be found in Doctor's Offices, Clinics, Hospitals, various stores, gas stations, and other places of vaccine administration. It is sad that the professional worries about getting the vaccine or injection into the patient but doesn't care about the handling and contamination of the sterile drug at the time of preparation and administration to the patient.

By contrast, this invention keeps the injection in an aseptic environment During preparation and all the way through administration to the patient.

SUMMARY OF THE INVENTION

The present invention includes an embodiment which will provide an aseptic environment area for the preparation of an aseptic or sterile unit and also provide the aseptic environment at the site of delivery or administration to the patient or customer.

The invention also provides an embodiment which is portable and can be easily relocated when needed.

DESCRIPTION OF THE FIGURES

The features of the invention believed to be novel and the elements characteristic of the invention are set forth with particularity in the claims. The figures are for illustration purposes only and are not drawn to scale. The invention itself, however, both as to organization and method of operation, may best be understood by reference to the detailed description that follows taken in conjunction with the accompanying drawings in which:

DETAILED DESCRIPTION OF THE INVENTION

This invention will now be described with reference to specific embodiments selected for illustration in the figures. It will be appreciated that the spirit and scope of this invention is not limited to the embodiments selected for illustration. Instead, the scope of this invention is defined separately in the appended claims. Also, it will be appreciated that the drawings are not rendered to any particular proportion or scale.

Figure 1:
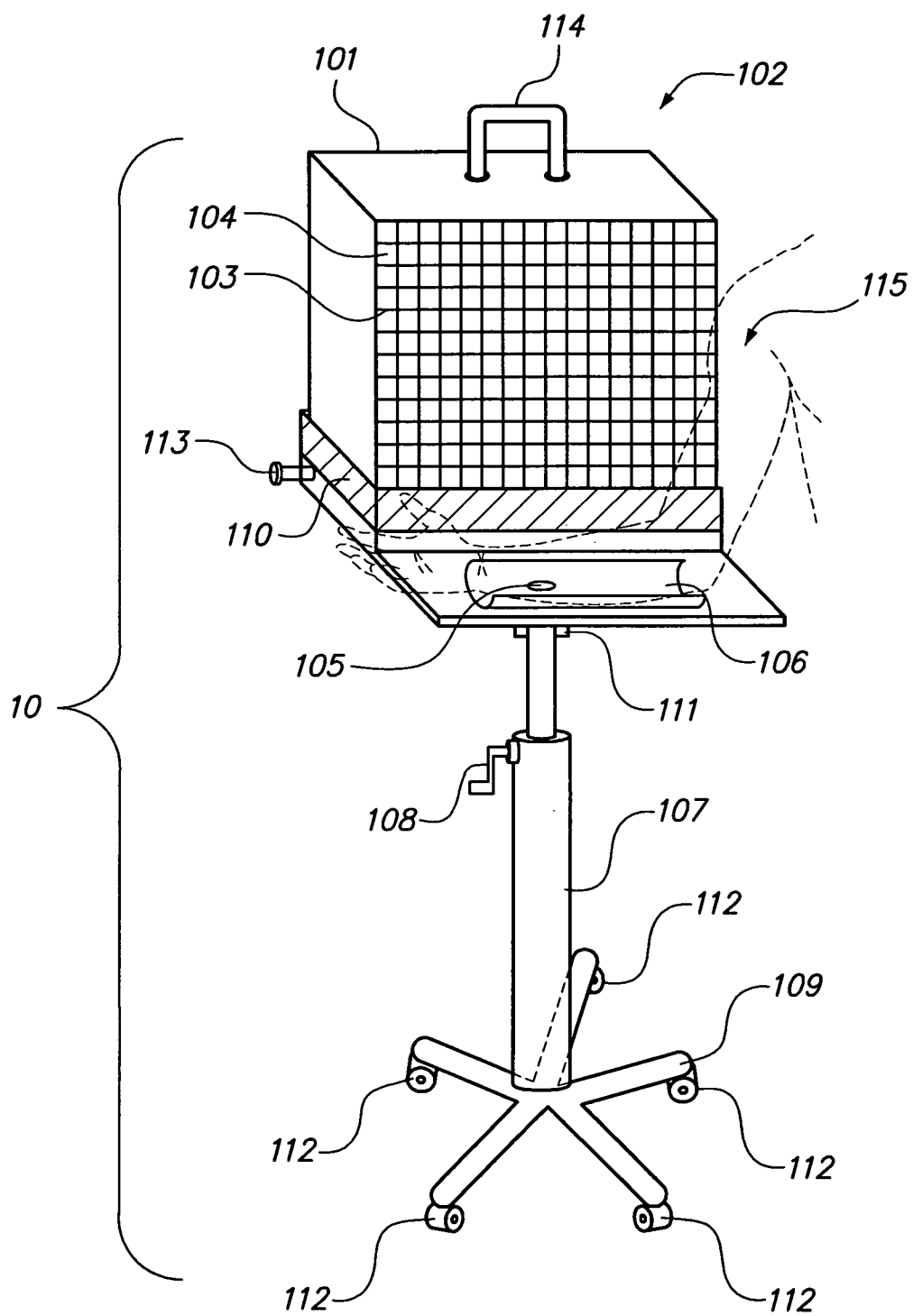
FIG. 1 is a front view of one embodiment of the present invention in which the embodiment shown is presented as a portable removable laminar flow unit inserted into the laminar flow holding means, the laminar flow holding means having a rotatable arm positioned attached, the laminar flow holding means attached to the upper part of an adjustable stand, whilst the adjustable stand extends into a secure base member which prevents the entire embodiment from tipping over.

FIG. 1 shows a front view of one of the envisioned Portable Aseptic Unit designated by the numeral "10". The Portable Aseptic Unit 10 consists of a series of parts including a Portable Removable Laminar Flow Unit 101 consisting of an Air Intake Member 102, HEPA Air Filtration Unit 103 and a Laminar Flow Aseptic Air Exhaust 104; the Portable Removable Laminar Flow Unit 101 being securely fitted into the Laminar Flow Holding Means 110 that also has attached to it a Rotatable Arm Positioner 106 with a Rotatable Attachment 105. The Laminar Flow Holding Means 110 is attached to the Adjustable Stand 107 by a Locking Swivel Pivot Member 111. The Laminar Flow Holding Means has attached to the Locking Swivel Pivot Member 111 an Adjustable Stand 107 with a Height Locking Means 108 located on it for height adjustment and a Secure Base Member located 109 located at the bottom with lockable casters 112. Attached to Laminar Flow Holding Means is a Locking Device 113 to hold the Portable Removable Laminar Flow Unit 101 securely in the Laminar Flow Holding Means 110. A Carrying Handle 114 is located on the Portable Removable Laminar Flow Unit 101. A phantom person's arm is shown as 115.

Figure 2:
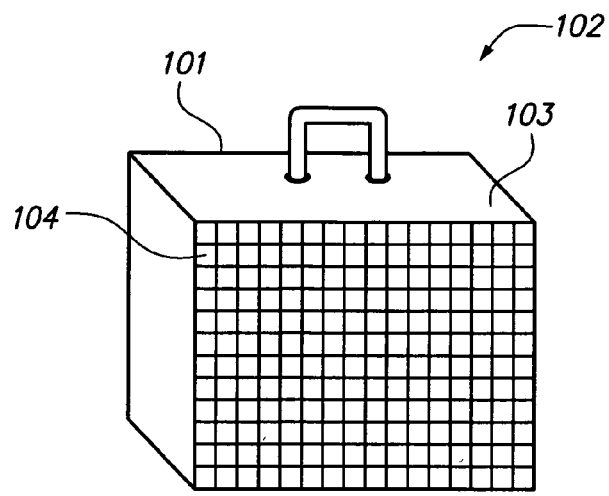
FIG. 2 is a front view of the portable removable laminar flow unit.

FIG. 2 is a front view of the Portable Removable Laminar Flow Unit 101 consisting of an Air Intake Member 102, HEPA Air Filtration Unit 103 and a Laminar Flow Aseptic Air Exhaust 104.

Figure 3:
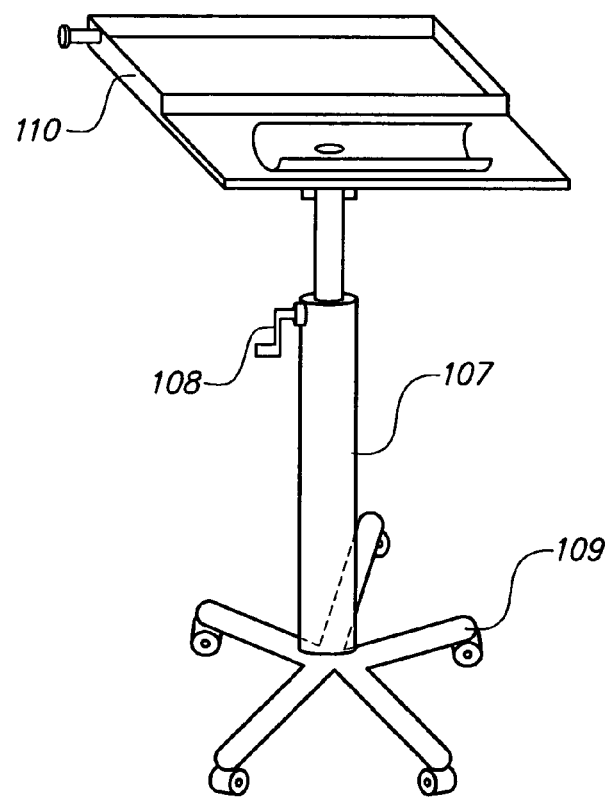
FIG. 3 is a front view of the laminar flow holding means, rotatable arm positioned, adjustable stand and secure base member.

FIG. 3 Shows a front view of the Adjustable Stand 107 Laminar Flow Holding Means 110 attached to the uppermost portion and with a Height Locking Means 108 located on it for height adjustment and a Secure Base Member located 109 located at the bottom.

REFERENCES CITED

| United States patents | | |
|---|---|---|
| 7,930,066 | April 2011 | Eliuk, et al. |
| 7,783,383 | August 2010 | Eliuk, et al. |
| 5,058,491 | October 1991 | Wiemer, et al. |
| 4,838,150 | June 1989 | Suzuki, et al. |
| 4,826,360 | May 1989 | Iwasawa et al. |
| 4,781,511 | November 1988 | Harada, et al. |
| 4,724,874 | February 1988 | Parikh, et al. |
| 4,587,793 | May 1986 | Brennan, et al. |
| 4,522,015 | June 1985 | Hildebolt |
| 4,372,100 | February 1983 | Miller, et al. |
| 4,332,122 | June 1982 | Williams |
| 3,815,315 | June 1974 | Glick |

Current U.S. Class: 53/425; 700/245; 53/111R; 53/428; 53/434
Current International Class: A61J 3/00 (20060101)
Field of Search: 53/425; 53/111R; 53/428; 53/434; 454/187; 454/49

I claim:
1. A portable aseptic unit comprising:
 a. a laminar flow unit comprising:
  i. an air intake member;
  ii. an air filtration unit; and
  iii. a laminar flow aseptic air exhaust; and
 b. an adjustable stand comprising:
  i. a laminar flow unit holding means having a recessed portion and a laterally adjacent non-recessed portion, the laminar flow unit holding means comprising a rotatable arm positioner configured to receive and position a subject's arm in front of the laminar flow aseptic air exhaust, wherein the laminar flow unit sits down in the recessed portion, and wherein the rotatable arm positioner is rotatably connected to the non-recessed portion and rotates relative to the laminar flow unit holding means;
  ii. a locking device attached to the laminar flow unit holding means that holds the laminar flow unit securely in the laminar flow unit holding means; and
  iii. a base member,
 wherein the laminar flow unit can be removed from the adjustable stand.

2. The portable aseptic unit of claim 1, wherein the adjustable stand further comprises a height locking means to adjust the height of the adjustable stand.

3. The portable aseptic unit of claim 1, wherein the adjustable stand further comprises a locking swivel pivot member.

4. The portable aseptic unit of claim 1, wherein the base member comprises lockable casters.

* * * * *